(12) United States Patent
Tateishi

(10) Patent No.: US 6,565,846 B2
(45) Date of Patent: *May 20, 2003

(54) MICROBIAL STRAINS OF PSEUDOMONAS, BACILLUS AND ENTEROBACTER/IN AGRICULTURAL CHEMICAL COMPOSITIONS

(75) Inventor: Hideaki Tateishi, Fukushima (JP)

(73) Assignee: Kureha Chemical Industry Co., Ltd., Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 22 days.

(21) Appl. No.: 09/486,391

(22) PCT Filed: Sep. 22, 1998

(86) PCT No.: PCT/JP98/04257

§ 371 (c)(1),
(2), (4) Date: Mar. 9, 2000

(87) PCT Pub. No.: WO99/16859

PCT Pub. Date: Apr. 8, 1999

(65) Prior Publication Data

US 2002/0051764 A1 May 2, 2002

(30) Foreign Application Priority Data

Sep. 26, 1997 (JP) .............................. 9-279609

(51) Int. Cl.$^7$ .............................. A01N 63/00; C12N 1/20
(52) U.S. Cl. ................ 424/93.4; 424/93.46; 424/93.47; 424/93.48; 435/252.1; 435/253.3; 435/252.9; 435/252.5
(58) Field of Search .............................. 424/93.4, 93.46, 424/93.47, 93.48; 435/252.1, 253.3, 252.9, 252.5

(56) References Cited

U.S. PATENT DOCUMENTS

| | | |
|---|---|---|
| 3,152,181 A | 10/1964 | Shapiro et al. |
| 3,835,057 A | 9/1974 | Cheng et al. |
| 4,163,800 A | 8/1979 | Wickett et al. |
| 4,714,563 A | 12/1987 | Kajs et al. |
| 5,607,980 A | 3/1997 | McAtee et al. |
| 5,681,802 A | 10/1997 | Fujiwara et al. |
| 5,686,089 A | 11/1997 | Mitra et al. |
| 5,968,539 A | 10/1999 | Beerse et al. |
| 6,183,757 B1 | 2/2001 | Beerse et al. |
| 6,183,766 B1 | 2/2001 | Sine et al. |

FOREIGN PATENT DOCUMENTS

| | | |
|---|---|---|
| JP | 4-104783 | 4/1992 |
| JP | 4-295407 | 10/1992 |
| JP | 6-133763 | 5/1994 |
| JP | 9-124426 | 5/1997 |
| JP | 9-124427 | 5/1997 |

OTHER PUBLICATIONS

Zhang, Ning; Pan, Naisui; Chen, ZhangliangCS Dep. Biol., Peking Univ., Beijing, 100871, Peop. Rep. ChinaSO Zhiwu Xuebao (1993), 35(5), 342–8.*
Poon et al., Bot Bull Acad Sin (Taipei), (1977), 18 (1), 61–70.*
Rao et al., Can J Microbiol, (1978) 24 (8), 1010–1012.*
Liu et al., Acta Bot Sin, (1991) 33 (2), 157–161.*
Li, et al., Curr. Plant Sci. Biotechnol. Agric. (1993), 15(Biotechnology in Agriculture), 439–43.*
Azegami, et al., Appl. Environ. Microbiol. (1988), 54(3), 844–7.*
ATCC Catalogue of Bacteria, 1996, pp. 132–143.*
Azegami, K., et al., "Pseudomonas plantarii sp. nov., the Causal Agent of Rice Seedling Blight", *International J. of Systematic Bacteriology* (1987), vol. 37, No. 2, pp. 144–152.
Azegami, K., et al., "Tropolone as a Root Growth–Inhibitor Produced by a Plant Pathogenic Pseudomonas sp. Causing Seedling Blight of Rice", *Ann. Phytopath. Soc.* Japan, vol. 51, No. 3, pp. 315–317.
Ponka, P., et al., "The Effect of Various Chelating Agents on the Mobilization of Iron from Reticulocytes in the Presence and Absence of Pyridoxal Isonicotinoyl Hydrazone", *Biochimica et Biophysica Acta*, (1984), vol. 802, No. 3, pp. 477–489.
Pitt, C.G., et al., "The Selection and Evaluation of New Chelating Agents for the Treatment of Iron Overload", *J. Pharmacol. Exp. Ther.* (1979), vol. 208, No. 1, pp. 12–18.

* cited by examiner

*Primary Examiner*—Irene Marx
(74) *Attorney, Agent, or Firm*—Hollander Law Firm, P.L.C.

(57) ABSTRACT

A method for screening a bacterium antagonistic to pathogenic bacteria that emerge during raising of seedlings of gramineous plants utilizing tropolone resistance and tropolone non-producing property as indices, and a microbial pesticide containing as an active ingredient the bacterium that has tropolone resistance and tropolone non-producing property selected by the screening method or spores thereof.

14 Claims, No Drawings

MICROBIAL STRAINS OF PSEUDOMONAS, BACILLUS AND ENTEROBACTER/IN AGRICULTURAL CHEMICAL COMPOSITIONS

TECHNICAL FIELD

The present invention relates to a method for screening microbes antagonistic to pathogenic bacteria that emerge during raising of seedlings of gramineous plants by selection from a plant body, soil, a seed or seed soaking water utilizing tropolone resistance and tropolone non-producing characteristics as indices. Also, the present invention relates to a microbial pesticide containing as an active ingredients a bacterium and spores thereof characterized by having a resistance to tropolone and not producing tropolone and also having a antagonistic activity against pathogenic bacteria that emerge during raising of seedlings of gramineous plants.

BACKGROUND ART

Diseases that emerge during raising of seedlings of gramineous plants include rice "Bakanae" disease, Helminthosporium leaf spot, and blast typically caused by fungi, rice bacterial gram rot, bacterial seedling blight, bacterial brown stripe, etc. caused by bacteria. To prevent these diseases, seed disinfectants, soil drenching agents, soil drench agents, foliage application agents after greening are said to be effective and these are used systematically by using them singly or incombination. For the disease damages by fungi, it has recently become possible to prevent them at high degree with EBI agents having high efficacy. Also, the disease damages caused by bacteria are prevented by use of chemical pesticides. However, chemical pesticides are generally low in their effect when bacterial diseases outburst and so that the problem remains that no sufficient prevention can be obtained. In case bacterial diseases outburst, at present the affected seedlings must be abolished. Therefore, development of a pesticide that can prevent or control the outburst of bacterial diseases has been desired.

Under the circumstances, the present inventors have made intensive investigation with view to making a research on bio-controlling material that is superior in controlling effect to chemical pesticides on the bacterial diseases of gramineous plants. Focusing on tropolone, which is a pathogenic toxin of pathogenic bacteria on rice bacterial seedling blight disease, they have searched a bacterium that is resistant to tropolone but does not produce tropolone from rice plants and established a method for screening a antagonistic bacteria to the pathogenic bacteria. Using this screening method, they have made an extensive search for microbial materials that can be used for controlling bacterial diseases. As a result, they have been successful in isolating antagonistic bacteria from rice seedlings that are antagonistic to the pathogenic bacteria.

DISCLOSURE OF THE INVENTION

The present invention relates to a method for screening a microbe antagonistic to pathogenic bacteria that emerge during raising of seedlings of gramineous plants by selecting a microbe from plant body, soil, seeds or seed soaking water utilizing tropolone resistance and tropolone non-producing property as indices. Also the present invention relates to a microbial pesticide containing as an active ingredient, the bacterium that is characterized by tropolone resistance and tropolone non-producing property selected by the screening method or spores thereof. Specifically, the present invention relates to a microbial pesticide comprising as a bacterium having a antagonistic action against pathogenic bacteria on rice plants, especially those that emerge during raising rice seedlings, a bacterium selected from the group consisting of bacteria belonging to the genera Pseudomonas, Bacillus, and Enterobacter. Also the present invention relates to a microbial pesticide comprising a mixture of two or more out of these. Specifically, the present invention relates to amicrobial pesticide for controlling bacterial diseases of gramineous plants, characterized in that one of bacteria belonging to either one of the genera Pseudomonas, Bacillus, and Enterobacter that have a antagonistic activity to pathogenic bacteria for bacterial diseases emerging in rice plants or a mixture of two or more of these is used for seed treatment or caused to be contained by soil for raising seedlings, or the bacterial cells are added to a seed soaking water, or the bacterium-containing solution is sprayed onto a rice plant body in the field.

BEST MODE FOR CARRYING OUT THE INVENTION

The screening method of the present invention is carried out by placing or spreading a fragment of a plant such as rice plant, homogenate of plant, soil, a seed, and a seed soaking water, on a suitable solid medium containing tropolone transplanting the resulting colonies of a tropolone resistant bacterium on a suitable solid medium containing iron ion, and selecting a colony that shows no red color on the iron-containing medium, cultivating the bacterium on a suitable medium to grow it, collecting the bacterial cells, converting the cells to a formulation or directly treating the infected seeds with a live bacterium suspension, and then raising seedlings and examining the protective activity to select an effective strain. In the screening of the present invention, tropolone derivatives may also be used instead of tropolone.

The bacterium that can be selected by the screening of the present invention and has a antagonistic activity to the pathogenic bacteria emerging during raising seedlings of gramineous plants, or spores of the bacterium can be utilized as an active ingredient of a microbial pesticide. The bio-controlling material that are used in the present invention are obtained by the above screening method and include, for example, bacteria belonging to either one of the genera Pseudomonas, Bacillus, and Enterobacter or two or more of them may be used in admixture. The bacterium belonging to the genus Pseudomonas includes, for example, *Pseudomonas aureofaciens,* and more specifically *Pseudomonas aureofaciens* B5. The bacterium belonging to the genus Bacillus includes, for example, *Bacillus polymyxa* and more specifically Bacillus is *Bacillus polymyxa* B36. The bacterium belonging to the genus Enterobacter includes, for example, *Enterobacter cloacae* and more specifically *Enterobacter cloacae* B51. The bacteriological characteristics of *Pseudomonas aureofaciens* B5, *Bacillus polymyxa* B36 and *Enterobacter cloacae* B51 will be indicated below.

TABLE 1

Characteristics of *Pseudomonas aureofaciens* B5

| Test Item | Results |
| --- | --- |
| Morphology | Bacillus |
| Gram stain | – |

TABLE 1-continued

Characteristics of *Pseudomonas aureofaciens* B5

| Test Item | Results |
|---|---|
| Spore | − |
| Mobility | + |
| Flagella | Extreme polytrichate |
| Oxygen requirement | Aerobic |
| Oxidase | + |
| Catalase | + |
| O/F | O |
| Color of colony | Not producing Characteristic pigment |
| Fluorescent pigment generation | + |
| Water-soluble pigment generation | + (Orange) |
| PHP accumulation | − |
| Growth at 41° C. | − |
| Levan generation | − |
| Arginine dihydrolase | + |
| Denitrification | − |
| Reduction of nitrate | − |
| Liquefaction of gelatin | + |
| Hydrolysis of starch | − |
| Decomposition of Tween 80 | + |
| Carbon source assimilation | |
| Glucose | + |
| Trehalose | + |
| 2-Ketogluconic acid | + |
| Inositol | + |
| Geraniol | − |
| L-Valine | + |
| β-Alanine | + |
| DL-Arginine | + |
| Adonitol | − |
| Sorbitol | − |
| Quinone system | Q-9 |
| GC Content in intracellular DNA (mol %) | 63 |

TABLE 2

Characteristics of *Bacillus polymyxa* B36

| Test Item | Results |
|---|---|
| Morphology | Bacillus |
| Gram stain | + |
| Spore | + |
| Shape | Ellipsodial |
| Position | Terminal |
| Sporangium | evaginating |
| Mobility | + |
| Oxygen requirement | Facultative aerobic |
| Catalase | + |
| Growth under anaerobic conditions | + |
| VP reaction | + |
| pH of VP broth | 4.7 |
| Acid formation from glucose | + |
| Gas formation from glucose | + |
| Liquefaction of gelatin | + |
| Hydrolysis of starch | + |
| Utilization of citrate | − |
| Utilization of propionate | − |
| Yolk reaction | + |
| Reduction of nitrate | − |
| Generation of dihydroxyacetone | + |
| Growth at pH 6.8 (nutrient broth) | + |
| Growth at pH 5.7 | + |
| Growth in the presence of 5% NaCl | − |
| Growth in the presence of 7% NaCl | − |
| Growth at 5° C. | − |
| Growth at 10° C. | + |
| Growth at 40° C. | + |
| Growth at 50° C. | − |
| GC Content in intracellular DNA (mol %) | 45 |

TABLE 3

Characteristics of *Enterobacter cloacae* B51

| Test Item | Results |
|---|---|
| Morphology | Bacillus |
| Gram stain | − |
| Mobility | + |
| Yellow pigment | − |
| Red pigment | − |
| Growth on McKonkey agar medium | + |
| Growth on Simmons citrate agar medium | + |
| Urease | − |
| Oxidase | − |
| H₂S (TSI) Generation | − |
| Reduction of nitrate | + |
| Utilization of malonate | + |
| ONPG | + |
| Arginine dihydrolase | + |
| Lysine decarboxylase | − |
| Ornithine decarboxylase | + |
| Casein hydrolysis | − |
| Dnase | − |
| Gas production from glucose | + |
| Acids: | |
| Mannit | + |
| Adnit | − |
| Arabinose | + |
| Inosit | − |
| Rhamnose | + |
| Sorbit | + |
| Maltose | + |
| Saccharose | − |
| IPA | − |
| VP Reaction | + |
| Indole production | − |

These three bacteria were isolated from rice seedlings by the present inventors. From the above characteristics, these were identified as *Pseudomonas aureofasciens*, *Bacillus polymyxa* and *Enterobacter cloacae* referring to Bergy's Manual of Systematic Bacteriology Vol. 1, Vol. 2, and Bergy's Manual of Systematic Bacteriology (Ninth Edition). The bacteria were named *Pseudomonas aureofaciens* B5, *Bacillus polymyxa* B36, and *Enterobacter cloacae* B51 respectively. The bacteria have been deposited at National Institute of Bioscience and Human Technology, Institute of Industrial Science and Technology, Ministry of International Trade and Industry under FERM BP-6067, FERM BP-6068, and FERM BP-6069.

The bacteria are resistant to tropolone and are tropolone non-producing. They have a antagonistic activity to bacteria emerging in gramineous plants, mainly pathogenic bacteria causing bacterial disease damages. Examples of disease damages against which they are effective include rice bacterial seedling blight (*Pseudomonas plantarii*), rice bacterial gram rot (*Pseudomonas glumae*), rice bacterial brown stripe (*Pseudomonas avenae*), rice bacterial leaf blight (*Xanthomonas campestris*), rice bacterial halo blight (*Pseudomonas syringae* pv. Oryzae), rice bacterial foot rot (*Erwinia chrysanthemi* pv. Zeae), rice bacterial palea browning (*Erwinia herbcola*), rice bacterial sheath brown rot (*Pseudomonas fuscovaginae*), rice "Bakanae" disease (*Gibberella fujikuroi*), rice Helminthosporium leaf spot (*Cochliobolas miyabeanus*), rice blast (*Pyricularia oryzae*), barley/wheat bacterial black node (*Pseudomonas syringae* pv. *japonica*), oat bacterial halo blight (*Pseudomonas syringae* pv. *coronafaciens*), oat bacterial stripe blight (*Pseudomonas syringae* pv. *striafaciens*), corn bacterial brown stripe (*Pseudomonas avenae*), corn bacterial stalk rot (*Erwinia chrysanthemi* pv. *zeae*), fescue/rye grass halo blight (*Pseudomonas syryngae* pv. *atropurprea*), sorghum bacterial leaf stripe (*Pseudomonas andropogonis*), Zoysia grass Rhizoctonia disease (*Rhizoctonia solani*), zoysia grass Rhizoctonia rot (Rhizoctonia) etc.

The microbial pesticide of the present invention comprises the bacteria and/or spores thereof as an active ingredient. Suspensions of the above bacteria are spread, sprayed, or coated on, for example, a gramineous plant or seeds thereof or gramineous plant seeds are dipped in the suspensions of the bacterial or the bacterial cells are added to seed soaking water, drenched or mixed in soil for raising seedlings (bed soil or cover soil), or the bacterial suspension is applied to the gramineous plant body in the field. Suitable concentrations of the bacteria may vary depending on the above methods of application. For example, in the case where rice seeds are subjected to dip treatment, it is conducted with the bacteria in a concentration of $1 \times 10^{11}$ to $1 \times 10^2$/ml, preferably $1 \times 10^{10}$ to $1 \times 10^5$/ml, at 5 to 40° C., preferably 15 to 30° C., for 1 to 2 days. In this case, the suspension may be a culture broth. Alternatively, the medium may be removed from the culture broth by, for example, centrifugation and the cells may be resuspended in water or physiological saline, buffer, etc. before use. Also, there may be used a solution obtained by resuspending cells that have been stored in a stable state by freeze-drying directly or with a suitable dispersant.

The microbial pesticide of the present invention may be one that is a suspension of the above antagonistic bacteria and/or spores thereof having a antagonistic activity to the pathogenic bacteria emerging during raising gramineous plant seedlings as they are. However, they may be mixed with various carriers such as a solid carrier or liquid carrier, and further with additives and other formulation aids, if necessary, and used as formulations prepared as wettable powder, suspension, powder, granule, paste, and microcapsule.

The solid carriers used upon formulation include, for example, mineral carriers such as kaolin clay, pyrophyllite, bentonite, montmorillonite, diatomaceous earth, acid white soil, vermiculite, and pearlite, and inorganic salts such as ammonium sulfate, ammonium phosphate, ammonium nitrate, urea, ammonium chloride, and calcium carbonate. Also, organic fine powders such as wheat flour, wheat bran, and rice bran may be used. The liquid carriers include vegetable oils such as soybean oil and cottonseed oil, glycerol, ethylene glycol, polyethylene glycol, propylene glycol, polypropylene glycol, etc.

The formulation of bonds and dispersants include polysaccharides such as casein, gelatin, starch, gum Arabic, alginic acid, and cellulose derivatives, lignin derivatives, saccharides, vegetable oils, mineral oils, synthetic water soluble polymers, etc.

Besides, as the formulation auxiliaries, there can be used anti-freezers, defoaming agents, thickening agents, etc., as needed.

The antagonistic bacteria of the present invention can be used in admixture with seed disinfectants or sprays for disease damages caused by fungi. For example, there can be cited ipconazol, pefurazoate, triflumizole, prochloraz, fludioxonil, benomyl, thiophanate-methyl, fthalide, tricyclazol, pyroquilon, carpropamid, ferimzone, isoprothiolane, EDDP, carboxine, etc. Further, the antagonistic bacteria of the present invention may be used with or without mixing with insecticides, nemotocides, acaricides, fungicides, herbicides, plant growth regulator, synergists, etc. simultaneously.

The formulations of the microbial pesticide of the present invention may contain usually about 0.1 to 95% by weight in a wet weight of the antagonistic bacteria of the present invention. It is preferred that the formulation contains about $10^3$ to about $10^{10}$ colonies per g of formulation.

EXAMPLE

Hereafter, the present invention will be described by Screening Example, Test Examples, and Formulation Example.

Screening Example
(Isolation of an Antagonistic Bacterium From a Rice Seedling)

An about 1 cm long section is cut from a ground contacting part of rice seedling infected with rice bacterial seedling blight and ground in a mortar with addition of a small amount of sterile water. The ground solution is appropriately diluted with sterile water. This is spread on a Potato Polypeptone Glucose Agar (PPGA) medium containing 100 ppm of tropolone, and incubated at 30° C. for 5 days. Colonies emerged are transplanted onto a PPGA medium to which is added ferric chloride so that $Fe^{+++}$ is 50 ppm and incubated at 30° C. for 5 days. If the colonies formed are composed of rice bacterial seedling blight pathogenic bacterium which produced tropolone, it presents red color since the tropolone forms a complex with $Fe^{+++}$. If the bacterium is tropolone non-producing one, no red color is presented. The colonies that present no red color are selected and cultivated in a PPG medium at 30° C. for 2 days with shaking and the medium is removed and separated by centrifugation at 5000×g for 30 minutes.

The obtained cells are resuspended in sterile water and rice seeds infected with bacterial seedling blight are dipped in the cell suspension at 20° C. for 24 hours. The treated rice seeds are soaked in water under appropriate conditions to stimulate germination and then seedlings thereof are raised. Comparing with the non-treated plot, bacterial strains that expressed protective effect are selected as a antagonistic bacterium.

Test Example 1
(Efficacy Test Against Rice Seedling Bacterial Seedling Blight Disease)

Rice seeds (caltivar: Nihonbare) inoculated with bacterial seedling blight pathogenic bacterium at the flowering stage and *Pseudomonas aureofaciens* B5, *Bacillus polymyxa* B36, and *Enterobacter cloacae* B51, bacteria obtained as above that are resistant to tropolone but produce no tropolone, were used to examine the efficacy of seed treatment on the rice bacterial seedling blight.

*Pseudomonas aureofaciens* B5, *Bacillus polymyxa* B36, and *Enterobacter cloacae* B51 as the antagonistic bacteria were each cultivated in a PPGA medium at 30° C. for 24 hours, the medium was removed therefrom by centrifugation, and the obtained cells were resuspended in sterile water before use. The infected seeds were dipped in a antagonistic bacteria suspension (cell concentration $1 \times 10^9$/ml) for 24 hours, followed by soaking the seeds in water at 30° C. for 3 days. The volumetric ratio of seeds to bacterial suspension or water was 1:1. Thereafter, the seeds were sown in a box (10×15 cm) for raising seedlings packed with commercially available granulated soil for raising rice seedlings (trade name: KUMIAI Granulated Soil). A population of 5 g of dry rice seed per box (3 repetitions per plot). Thereafter, the culture soil was kept in an incubator at 32° C. for 4 days. Thereafter, the seedlings were raised in a glass greenhouse. 15 days after the sewing, the incidence of disease in each test plot was evaluated based on the following indices. For comparison, similar tests were conducted using a 200 fold diluted solution of Sporutak-Starner SE, commercially available seed disinfectant. The results obtained are shown in Table 4.

0: No disease,
1: Occurrence of chlorosis of seedlings was observed but no damping off seedling was observed,
2: 25% or fewer damping off seedlings,
3: 25 to 50% of damping off seedlings,
4: 50 to 80% of damping off seedlings, and
5: 80% or more of damping off seedlings (almost all were dead).

TABLE 4

Effect of Each Strain on Rice Bacterial Seedling Blight

| Name of Strain or Name of Chemical | Incidence Index |
|---|---|
| *Pseudomonas aureofaciens* B5 | 0.0 |
| *Bacillus polymyxa* B36 | 0.3 |
| *Enterobacter cloacae* B51 | 0.3 |
| Sportak-Starner SE (200-fold dilution) | 2.3 |
| No treatment | 4.0 |

Test Example 2
(Efficacy Test on Rice Bacterial Seedling Rot)

Rice seeds (caltivar: Nihonbare) inoculated with rice bacterial seedling rot pathogenic bacterium under reduced pressure and *Pseudomonas aureofaciens* B5 as a antagonistic bacterium were used and the protective effect of treatment of seeds with the antagonistic bacterium was examined. The test was conducted in a method similar to that in Test Example 1. Evaluation was made based on sighted view indices taking the number of withered seedlings in the no treatment plot after 15 days after the sewing as 5. The results obtained are shown in Table 5.

TABLE 5

Effect of Each Strain or Chemicals on Rice Bacterial Seedling Rot

| Name of Strain or Name of Chemical | Incidence Rate |
|---|---|
| *Pseudomonas aureofaciens* B5 | 1.5 |
| Sportak-Starner SE (200-fold dilution) | 2.4 |
| No treatment | 5.0 |

Formulation Example

The antagonistic bacterium of the present invention is cultivated in a suitable liquid medium with shaking and then the medium components are removed by centrifugation. To this is added kaolin clay and water or a suitable buffer to resuspend, followed by freeze-drying. This is mildly pulverized in a mortar. The pulverized powder (85% by weight) is mixed with 10% of polyoxyethylene nonyl phenyl ether and 5% of sodium ligninsulfonate to obtain a formulation in the form of wettable powder.

Industrial Applicability

The microbial pesticide containing as an active ingredient the bacteria and spores thereof selected by the screening method of the present invention can be expected to exhibit higher efficacy than chemical pesticides and be effective to those bacteria resistant to specified chemical pesticides. Therefore, its application alternative to the conventional chemical pesticides can reduce the release of chemical substances in the environment. According to the present invention, economical losses that farmers suffer by the emergence of bacterial disease damages on gramineous plants can be alleviated.

Reference to Microbes
1) Depositary Institution: National Institute of Bioscience and Human Technology, Institute of Industrial Science and Technology, Ministry of International Trade and Industry Address: No. 1–3, Higashi 1-chome, Tsukuba-shi, Ibaraki-ken, Japan
Date of Deposition: Aug. 21, 1997
Deposition Number: FERM BP-6067
2) Depositary Institution: National Institute of Bioscience and Human Technology, Institute of Industrial Science and Technology, Ministry of International Trade and Industry Address: No. 1–3, Higashi 1-chome, Tsukuba-shi, Ibaraki-ken, Japan
Date of Deposition: Aug. 21, 1997
Deposition Number: FERM BP-6068
3) Depositary Institution: National Institute of Bioscience and Human Technology, Institute of Industrial Science and Technology, Ministry of International Trade and Industry Address: No. 1–3, Higashi 1-chome, Tsukuba-shi, Ibaraki-ken, Japan
Date of Deposition: Aug. 21, 1997
Deposition Number: FERM BP-6069

What is claimed is:
1. A microbial pesticide, comprising:
a carrier; and
as an active ingredient, at least one biologically pure culture of a bacteria strain selected from the group consisting of *Pseudomonas aureofaciens* B5, FERM BP-6067, *Bacillus polymyxa* B36, FERM BP-6068 and *Enterobacter cloacae* B51, FERM BP-6069.
2. The microbial pesticide according to claim 1, wherein the active ingredient is *Pseudomonas aureofaciens* B5, FERM BP-6067.
3. The microbial pesticide according to claim 1, wherein the active ingredient is *Bacillus polymyxa* B36, FERM BP-6068.
4. The microbial pesticide according to claim 1, wherein the active ingredient is *Enterobacter cloacae* B51, FERM BP-6069.
5. A microbial pesticide according to claim 1 which comprises two or more of said biologically pure cultures.
6. A biologically pure culture of a bacteria strain having all the identifying characteristics of *Pseudomonas aureofaciens* B5, FERM BP-6067.
7. A biologically pure culture of a bacteria strain *Pseudomonas aureofaciens* B5, FERM BP-6067 according to claim 6 which bacteria is antagonistic to pathogens that cause disease in gramineous plant seedlings and which is obtained by a process comprising:
placing or spreading on a solid medium containing 100 ppm tropolone at least one source of bacteria to be screened selected from the group consisting of a gramineous plant body, soil used to raise a gramineous plant seedling, a gramineous plant seed, a homogenate of a gramineous plant seed, and gramineous plant seed soaking water to form bacterial colonies, transplanting said bacterial colonies to a solid medium containing 50 ppm $Fe^{+++}$, and recovering a colony that is not red.

8. A biologically pure culture of a bacteria strain according to claim 6, wherein said bacteria strain is *Pseudomonas aureofaciens* B5, FERM BP-6067.

9. A biologically pure culture of a bacteria strain having all the identifying characteristics of *Bacillus polymyxa* B36, FERM BP-6068.

10. A biologically pure culture of a bacteria strain *Bacillus polymyxa* B36, FERM BP-6068 according to claim 9 which bacteria is antagonistic to pathogens that cause disease in gramineous plant seedlings and which is obtained by a process comprising:

placing or spreading on a solid medium containing 100 ppm tropolone at least one source of bacteria to be screened selected from the group consisting of a gramineous plant body, soil used to raise a gramineous plant seedling, a gramineous plant seed, a homogenate of a gramineous plant seed, and gramineous plant seed soaking water to form bacterial colonies, transplanting said bacterial colonies to a solid medium containing 50 ppm $Fe^{+++}$, and recovering a colony that is not red.

11. A biologically pure culture of a bacteria strain according to claim 9, wherein said bacteria strain is *Bacillus polymyxa* B36, FERM BP-6068.

12. A biologically pure culture of a bacteria strain having all the identifying characteristics of *Enterobacter cloacae* B51, FERM BP-6069.

13. A biologically pure culture of a bacteria strain *Enterobacter cloacae* B51, FERM BP-6069 according to claim 12 which bacteria is antagonistic to pathogens that cause disease in gramineous plant seedlings and which is obtained by a process comprising:

placing or spreading on a solid medium containing 100 ppm tropolone at least one source of bacteria to be screened selected from the group consisting of a gramineous plant body, soil used to raise a gramineous plant seedling, a gramineous plant seed, a homogenate of a gramineous plant seed, and gramineous plant seed soaking water to form bacterial colonies, transplanting said bacterial colonies to a solid medium containing 50 ppm $Fe^{+++}$, and recovering a colony that is not red.

14. A biologically pure culture of a bacteria strain according to claim 12, wherein said bacteria strain is *Enterobacter cloacae* B51, FERM BP-6069.

\* \* \* \* \*